United States Patent
Doerr

(10) Patent No.: US 9,459,305 B2
(45) Date of Patent: Oct. 4, 2016

(54) IMPLANTABLE MEDICAL DEVICE AND METHOD FOR MONITORING THE INSULATION OF AN ELECTRODE LINE OF SUCH A MEDICAL DEVICE

(71) Applicant: BIOTRONIK SE & CO. KG, Berlin (DE)

(72) Inventor: Thomas Doerr, Berlin (DE)

(73) Assignee: BIOTRONIK SE & CO. KG, Berlin (DE)

(*) Notice: Subject to any disclaimer, the term of this patent is extended or adjusted under 35 U.S.C. 154(b) by 59 days.

(21) Appl. No.: 14/463,515

(22) Filed: Aug. 19, 2014

(65) Prior Publication Data

US 2015/0061697 A1   Mar. 5, 2015

Related U.S. Application Data

(60) Provisional application No. 61/871,318, filed on Aug. 29, 2013.

(51) Int. Cl.
| | |
|---|---|
| *G01R 31/02* | (2006.01) |
| *A61N 1/37* | (2006.01) |
| *G01R 31/28* | (2006.01) |
| *A61N 1/375* | (2006.01) |
| *A61N 1/372* | (2006.01) |
| *A61N 1/08* | (2006.01) |

(52) U.S. Cl.
CPC ............. *G01R 31/025* (2013.01); *A61N 1/37* (2013.01); *G01R 31/282* (2013.01); *A61N 1/3752* (2013.01); *A61N 1/37258* (2013.01); *A61N 2001/083* (2013.01)

(58) Field of Classification Search
CPC ........................... G01R 31/025; G01R 31/282
USPC ........................................................ 324/551
See application file for complete search history.

(56) References Cited

U.S. PATENT DOCUMENTS

| | | | |
|---|---|---|---|
| 7,454,249 B1 | 11/2008 | Bornzin et al. | |
| 2003/0004552 A1 | 1/2003 | Plombon et al. | |
| 2011/0160808 A1 | 6/2011 | Lyden | |
| 2013/0325080 A1* | 12/2013 | Kroll | A61N 1/3925 607/6 |

OTHER PUBLICATIONS

European Search Report received from EP Application Serial No. 14174638.8, dated Jan. 14, 2015, 5 pages.

* cited by examiner

*Primary Examiner* — Thomas F Valone
(74) *Attorney, Agent, or Firm* — Arc IP Law, PC; Joseph J. Mayo

(57) ABSTRACT

An implantable medical device including at least one electrode line having an electrode pole, an electrode feed line, a counter electrode to the at least one electrode line, and an insulation sleeve. The insulation sleeve surrounds the electrode feed line and provides insulation between the electrode feed line and an electrolyte formed by bodily fluid. The electrode feed line and the electrode pole(s) include different materials, wherein the materials are different based on electrochemical series. The implantable medical device includes an insulation test unit having a DC voltage detector arranged between the electrode pole and the counter electrode, in order to detect an electrochemical voltage produced in the event of an insulation fault of the insulation sleeve due to defective contact between the electrolyte and the electrode feed line.

7 Claims, 1 Drawing Sheet

IMPLANTABLE MEDICAL DEVICE AND METHOD FOR MONITORING THE INSULATION OF AN ELECTRODE LINE OF SUCH A MEDICAL DEVICE

This application claims the benefit of U.S. Provisional Patent Application 61/871,318 filed on 29 Aug. 2013, the specification of which is hereby incorporated herein by reference.

BACKGROUND OF THE INVENTION

1. Field of the Invention

Embodiments of the invention generally relate to an implantable medical device and method for monitoring insulation of an electrode line of the implantable medical device. The implantable medical device includes at least one electrode line having an electrode pole, an electrode feed line, an insulation sleeve and a counter electrode to the electrode line. The insulation sleeve surrounds the electrode feed line and provides insulation between the electrode feed line and an electrolyte formed by bodily fluid.

2. Description of the Related Art

Generally, typical implantable medical devices demonstrate problems with regard to tightness between insulation sleeves of electrode feed lines, for example due to damage of the insulation sleeve or due to openings and gaps in joints between different insulation sleeve portions. Such insulation faults, typically, may, inter alia, produce falsifications of cardiological signals recorded by the electrode line, for example in the case of a cardiac pacemaker, wherein the function of the cardiac pacemaker may be impaired.

Known devices and methods for electrode fault detection are generally implemented to measure and evaluate different parameters, such as electrode impedances, signal amplitudes, interfering signal detection, stimulus thresholds, frequency analyses, various plausibility tests, etc. For example, United States Patent Publication 2011/0160808 to Lyden et al., entitled "Implantable Medical Device Including Isolation Test Circuit", appears to disclose an electrode fault detection system based on an impedance measurement. According to Lyden et al., as an alternative verification method to using impedance measurement, a current pulse may be fed between two electrodes and a response signal resulting therefrom, such as a voltage occurring between electrode lines, may be measured.

Generally, known devices and methods for electrode fault detection often demonstrate insufficient sensitivity and specificity. Typically, using an impedance measurement test may not sufficiently and reliably determine insulation faults, since the impedance of the actual electrode poles lies far below the impedance of an insulation fault, and therefore the insulation fault only causes an insignificant impedance drop in the impedance measurement test.

Reliable detection of an insulation fault at an implanted electrode line is therefore of great importance for the functional capability of such an implantable medical device, thus there is a need for an implantable medical device and method for monitoring the insulation of an electrode line of such a medical device.

BRIEF SUMMARY OF THE INVENTION

One or more embodiments of the invention are related to an implantable medical device with an electrode line, wherein an insulation fault in the region of the electrode line may be identified reliably, efficiently and promptly.

In at least one embodiment, the implantable medical device includes at least one electrode line having an electrode pole, an electrode feed line and an insulation sleeve. In one or more embodiments, the electrode feed line and the electrode pole(s) include different materials that differ based on electrochemical series. By way of at least one embodiment, the implantable medical device may include a counter electrode to the electrode line, and an insulation test unit having a direct current (DC) voltage detector arranged between the electrode pole and the counter electrode. By way of one or more embodiments, the insulation test unit may detect an electrochemical voltage produced in the event of an insulation fault of the insulation sleeve, due to defective contact between an electrolyte (formed by bodily fluid) and the electrode feed line.

At least one embodiment of the invention is related to a method for monitoring the insulation of the electrode line of the implantable medical device. One or more embodiments of the invention include providing the implantable medical device, measuring the voltage between the electrode pole and the counter electrode using the DC voltage detector, and evaluating the measured voltage in order to detect an electrochemical voltage produced in the event of an insulation fault of the insulation sleeve due to the defective contact between the electrolyte and the electrode feed line, using the insulation test unit having the DC voltage detector.

At least one embodiment of the invention is based on a physical-chemical effect, wherein the physical-chemical effect does not appear if the insulation sleeve is fully intact (non-defective) and therefore does not influence the actual measurement functions of the implantable medical device. According to one or more embodiments, if an insulation fault occurs, the insulation fault may impair the functional capability of the device. In at least one embodiment, a significant voltage change, such as a change in the measured voltage, is evaluated using the insulation test unit, and an electrochemical voltage, or change thereof, is detected to detect any insulation faults.

In one or more embodiments, the implantable medical device may include an electrically conductive housing that may include the counter electrode. In at least one embodiment, the counter electrode may be part of the insulation test unit. In one or more embodiments, at least a portion of the electrically conductive housing of the implantable medical device may form the counter electrode.

By way of at least one embodiment, the different materials of the electrode feed line and the electrode pole may include a material pairing, wherein the material pairing includes a combination of two materials selected from gold, platinum, silver and copper, or includes a combination of two materials selected from titanium, aluminum, chromium and MP35N.

According to at least one embodiment, the implantable medical device may include a signaling device coupled to the DC voltage detector. In one or more embodiments, the signaling device may display the insulation fault. The signaling device, by way of at least one embodiment, may include one or more of an optical warning device, such as a light, and an acoustic signal transmitter. In one or more embodiments, the signaling device may deliver a warning signal if the electrochemical voltage indicating an insulation fault is detected.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
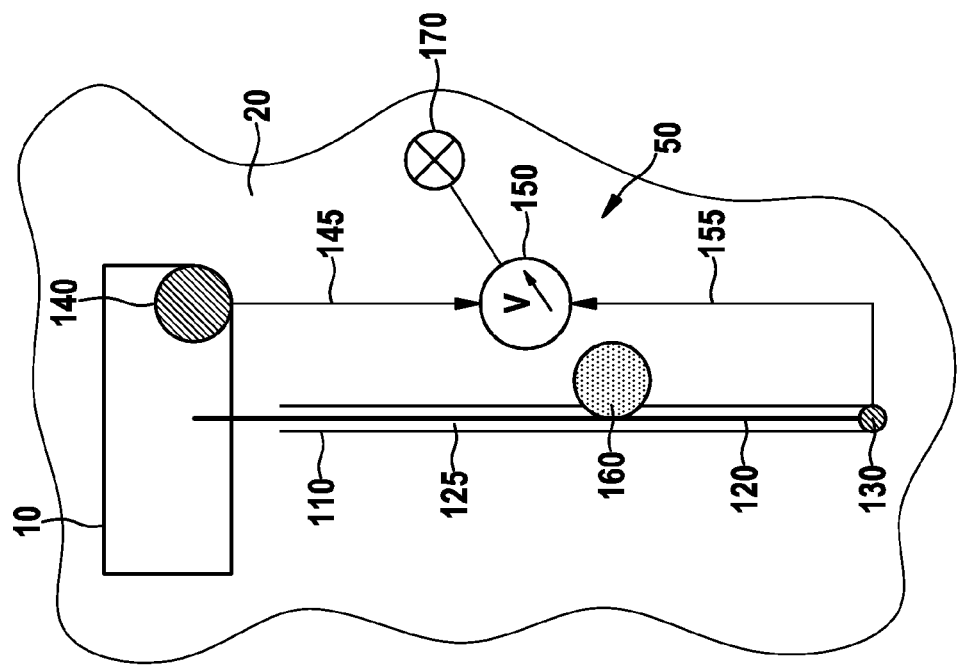
FIGS. 1 and 2: show schematic illustrations of an implanted medical device having an insulation sleeve and an insulation test unit, demonstrating when the insulation sleeve is functioning correctly (FIG. 1) and in the event of an insulation fault (FIG. 2).
Figure 2:
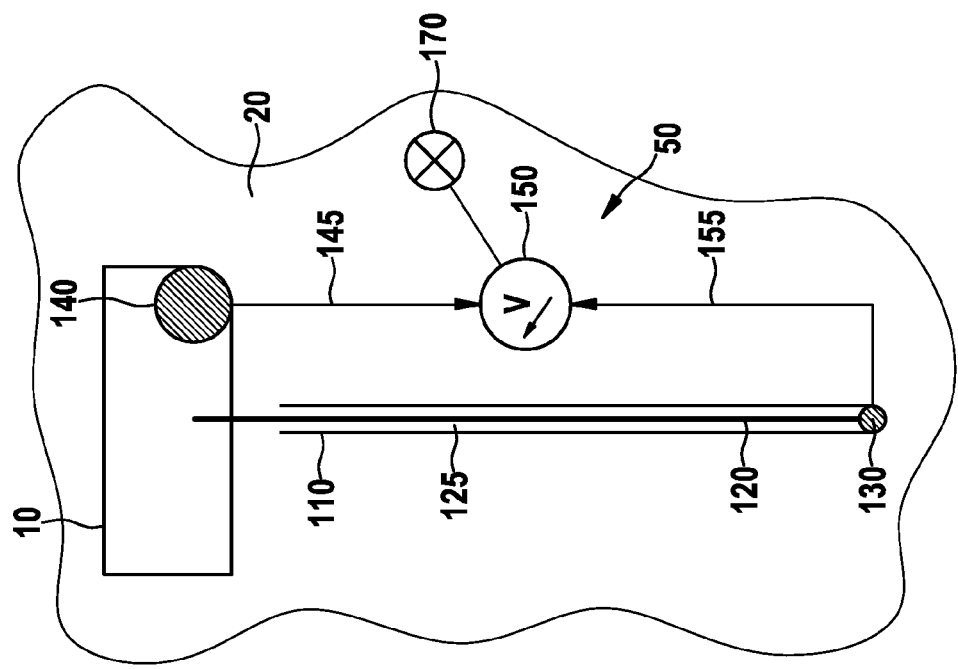

FIGS. 1 and 2 show schematic illustrations of an implanted medical device having an insulation sleeve and an insulation test unit, demonstrating when the insulation sleeve is functioning correctly (FIG. 1) and in the event of an insulation fault (FIG. 2).

As shown in FIGS. 1 and 2, one or more embodiments of the invention include an implantable medical device 10, such as an active electronic implant or a cardiac pacemaker, implanted into a human body 20. In at least one embodiment, the implantable medical device or cardiac pacemaker 10 includes an electrode pole 130 and at least one electrode line 110, wherein the at least one electrode line 110 may be introduced into a right ventricle of the heart, and may be anchored in the right ventricle of the heart via the electrode pole 130. In one or more embodiments, the implantable medical device includes at least one electrode feed line 120 as an electrical connection between the electrode pole 130 and the cardiac pacemaker 10. In at least one embodiment, the implantable medical device 10 may include an insulation sleeve 125, wherein the at least one electrode feed line may be surrounded, over its length, by the insulation sleeve 125.

The at least one electrode feed line 120 and the electrode pole 130, according to at least one embodiment, may include a material pairing of two different materials or metals, such as copper and gold, wherein the two different materials differ based on electrochemical series, and may have considerably different standard potentials in the electrochemical series. According to one or more embodiments, if the insulation sleeve 125 is intact, or non-defective, the material pairing may have no effect on stimulus potentials of the heart measured via the electrode pole 130.

By way of at least one embodiment, to monitor an intact, or non-defective, state of the insulation sleeve 125, the implantable medical device 10 may include an insulation test unit 50 and a counter electrode or pole 140. In one or more embodiments, the insulation test unit 50 may include a direct current (DC) voltage detector 150, such as a voltmeter. In at least one embodiment, the DC voltage detector 150 is arranged between the electrode pole 130 and the counter electrode pole 140 using one or more electrode connection lines 145 and 155. According to one or more embodiments, the DC voltage detector 150 may detect a voltage V produced between the electrode pole 130 and the counter pole 140. The voltage V, in at least one embodiment, due to the material pairing of the electrode feed line 120 and the electrode pole 130, occurs significantly if the insulation sleeve 125 is faulty, such as defective or not intact. As such, in one or more embodiments, a contact is established between the electrode feed line 120 and an electrolyte 160 (formed by the bodily fluid present in the body 20), as shown in FIG. 2. In at least one embodiment of the invention, in the event of an insulation fault, an electrochemical voltage is produced and may be detected by the DC voltage detector 150. According to one or more embodiments, the implantable medical device may include a signaling device 170, wherein the electrochemical voltage may be displayed via the signaling device 170 to a user of the implantable medical device 10. By way of at least one embodiment of the invention, the insulation fault of the insulation sleeve 125 of the at least one electrode line 110 may be detected in a reliable and efficient manner.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable medical device comprising
at least one electrode line having an electrode;
an electrode feed line;
an insulation sleeve;
   wherein said insulation sleeve is configured to
      surround said electrode feed line, and
      provide insulation between the electrode feed line and an electrolyte formed by bodily fluid;
a counter electrode to the at least one electrode line;
an insulation test unit comprising a direct current (DC) voltage detector arranged between the electrode and the counter electrode;
   wherein the counter electrode is part of the insulation test unit,
   wherein the DC voltage detector is configured to measure a voltage between the electrode and the counter electrode,
   wherein the electrode feed line and the electrode comprise different materials, wherein said different materials differ based on electrochemical series, and,
   wherein the insulation test unit is configured to evaluate the measured voltage and detect an electrochemical voltage produced in the event of an insulation fault of the insulation sleeve due to defective contact between the electrolyte and the electrode feed line; and,
a signaling device coupled to the DC voltage detector, wherein said signaling device is configured to
   output a warning signal to display said insulation fault, and,
   display the electrochemical voltage.

2. The implantable medical device as claimed in claim 1, further comprising an electrically conductive housing, wherein said electrically conductive housing comprises the counter electrode.

3. The implantable medical device as claimed in claim 1, wherein the different materials of the electrode feed line and the electrode comprise a material pairing, wherein the material pairing comprises
   a combination of two materials of gold, platinum, silver and copper, or
   a combination of two materials of titanium, aluminum, chromium and MP35N.

4. The implantable medical device as claimed in claim 2, wherein the different materials of the electrode feed line and the electrode comprise a material pairing, wherein the material pairing comprises
- a combination of two materials of gold, platinum, silver and copper, or
- a combination of two materials of titanium, aluminum, chromium and MP35N.

5. A method for monitoring the insulation of an electrode line of an implantable medical device comprising:
- providing an implantable medical device, wherein the implantable medical device comprises
  - at least one electrode line having an electrode pole;
  - an electrode feed line;
  - an insulation sleeve;
    - wherein said insulation sleeve is configured to surround said electrode feed line, and
      - provide insulation between the electrode feed line and an electrolyte formed by bodily fluid; and,
  - a counter electrode to the electrode line; and,
  - an insulation test unit comprising a direct current (DC) voltage detector arranged between the electrode pole and the counter electrode,
    - wherein the counter electrode is part of the insulation test unit;
- measuring a voltage between the electrode pole and the counter electrode with said DC voltage detector;
- evaluating the measured voltage and detecting an electrochemical voltage produced in the event of an insulation fault of the insulation sleeve due to defective contact between the electrolyte and the electrode feed line, with said insulation test unit; and,
- outputting a warning signal with a signaling device to display said insulation fault and display the electrochemical voltage.

6. The implantable medical device as claimed in claim 1, wherein said signaling device coupled to the DC voltage detector comprises one or more of an optical warning device and an acoustic signal transmitter.

7. The method as claimed in claim 5, wherein said signaling device coupled to the DC voltage detector comprises one or more of an optical warning device and an acoustic signal transmitter.

* * * * *